US00PP33349P2

(12) United States Plant Patent
Olesen

(10) Patent No.: US PP33,349 P2
(45) Date of Patent: Aug. 17, 2021

(54) MINIATURE ROSE PLANT NAMED 'POULTY025'

(50) Latin Name: *Rosa hybrida*
Varietal Denomination: Poulty025

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/974,006

(22) Filed: Sep. 3, 2020

(51) Int. Cl.
*A01H 5/02* (2018.01)
*A01H 6/74* (2018.01)

(52) U.S. Cl.
USPC ..... Plt./119

(58) Field of Classification Search
USPC ..... Plt./101, 116, 119, 123, 126
See application file for complete search history.

*Primary Examiner* — Susan McCormick Ewoldt

(57) ABSTRACT

A new garden rose plant of the Miniature class which has abundant, orange red flowers and attractive foliage. This new and distinct variety has shown to be uniform and stable in the resulting generations from asexual propagation.

2 Drawing Sheets

Botanical designation: *Rosa hybrida.*
Variety denomination: 'Poulty025'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulty025', originated as a single seedling from the stated cross.

The new variety may be distinguished from its male pollen parent and female seed parent primarily by the following characteristics. The male pollen parent plant has red purple flowers while the new variety has orange red flowers. The female seed parent plant has a growth height of 75 to 100 cm, while the new variety has a growth height of 39 cm.

The objective of the hybridization of this rose variety was to create a new and distinct variety with unique qualities, such as:

1. Uniform and abundant orange red flowers;
2. Vigorous, but compact growth when propagated on its own roots;
3. Exceptional disease resistance.

This combination of qualities is not present in previously available commercial cultivars of this type, known to the inventor, and distinguish 'Poulty025' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulty025' was selected in the spring of 2010 by the inventor as a single plant from the progeny of the aforementioned hybridization.

Asexual reproduction of 'Poulty025' by rooted cuttings was first done by Mogens N. Olesen in the nursery in Fredensborg, Denmark in July, 2010. This initial and other subsequent asexual propagations conducted in controlled environments have demonstrated that the characteristics of 'Poulty025' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty025'.

Specifically illustrated in FIG. 1 of the drawings are open flowers at various stages of development, viewed from above and the side, sepals and petals detached, showing reproductive flower parts and receptacle characteristics.

Figure 1:
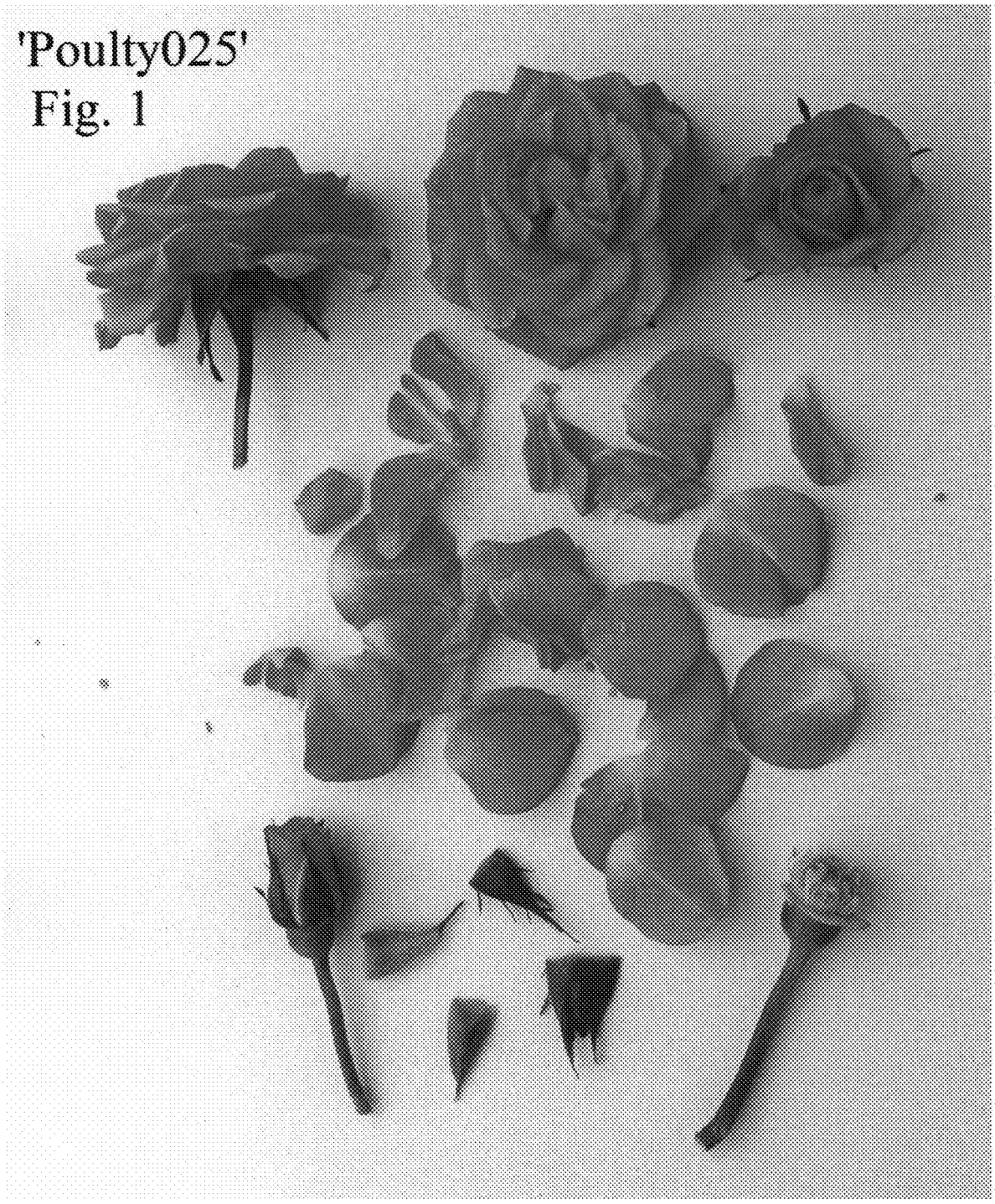
Figure 2:
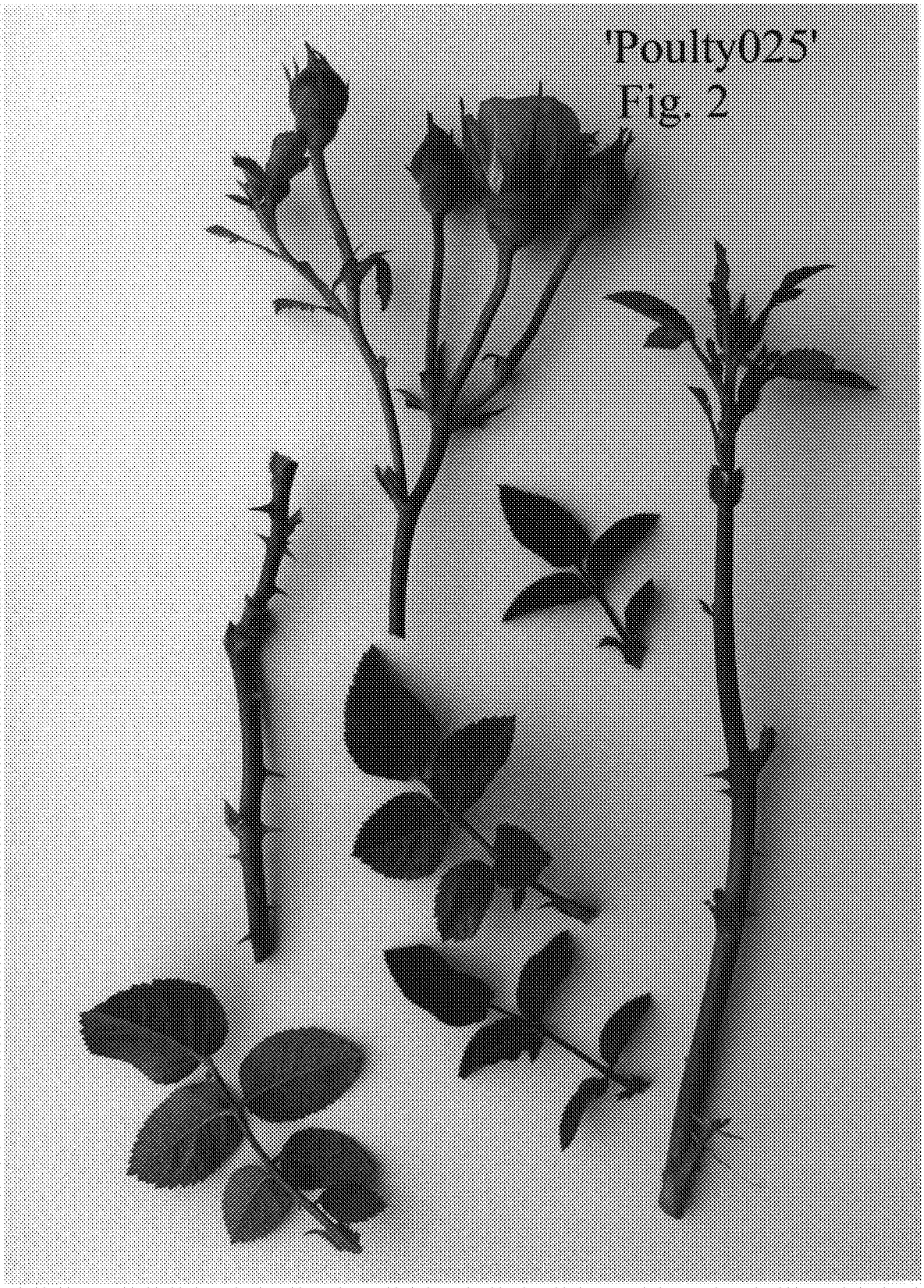

Specifically illustrated in FIG. 2 of the drawings are a cluster of flower buds opening on the branch, mature bare stem, juvenile bare stem, mature leaves, and juvenile leaves. Plants shown are 2 years of age.

DETAILED DESCRIPTION OF THE VARIETY

The following is a description of 'Poulty025', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulty010', U.S. Plant Pat. No. 24,872 are compared to 'Poulty025' in Chart 1.

CHART 1

| | 'Poulty025' | 'Poulty010' |
|---|---|---|
| Petal Count | 30 | 35 |
| Flower Diameter | 50 mm | 45 mm |
| General Tonality of Flower Color | Orange-Red Group N30B | Red Group 33A |

FLOWER AND FLOWER BUD

Blooming habit: Continuous.

Flower bud:

*Size.*—Upon opening, 26 mm in length from base of receptacle to end of bud. Bud diameter is 16 mm.

*Bud form.*—Urceolate.

*Bud color.*—As sepals divide petals are Orange-Red Group N30B and N30A.

*Sepal inner surface.*—Color: Yellow-Green Group 144B. Surface: Lightly pubescent.

*Sepal outer surface.*—Color: Yellow-Green Group 144A with strong intonations of Greyed-Purple Group 183A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 10 mm wide.

*Receptacle.*—Texture: Smooth. Size: 7 mm in height, 10 mm wide. Color: Yellow-Green Group 144A with intonations of Greyed-Purple Group 183C. Shape: Campanulate.

*Pedicel.*—Surface: Smooth. Length: 24 mm. Diameter: 2.5 mm. Color: Yellow-Green Group 144A with intonations of Greyed-Red Group 180A. Strength: Strong.

*Peduncle.*—Length: 1 to 2 cm. Diameter: About 3 mm. Color: Yellow-Green Group 145A. Texture: Smooth.

Flower bud development: Flower buds are borne in clusters of 3 on average.

Flower bloom:

*Fragrance.*—Moderate.

*Duration.*—The blooms have a 20 days. Petals fall cleanly away from plant after flowers have fully matured.

*Size.*—Flower diameter is 50 mm when open. Flower depth is 20 mm.

*Flower shape.*—High centered, semi double, with a high pointed center which is tightly closed.

*Shape of flower, side view.*—The upper portion is flat convex. The lower portion is concave.

Petalage: Under normal conditions, flowers have about 30 petals.

General tonality of flower: Open flowers are Orange-Red Group N30B.

Petal color:

*Upon opening, outer petals.*—Upper surface: Orange-Red Group N30B. Lower surface: Red Group 43C splashed with Red Group 43B.

*Upon opening, inner petals.*—Upper surface: Orange-Red Group N30B. Lower surface: Red Group 43C splashed with Red Group 43B.

*Basal petal spots, upon opening.*—Upper surface: Yellow Group 7A. Lower surface: Yellow Group 7A.

*After opening, outer petals.*—Upper surface: Orange-Red Group N30C. Lower surface: Red Group 41B.

*After opening, inner petals.*—Upper surface: Orange-Red Group N30C. Lower surface: Red Group 41B.

*Basal petal spots, after opening.*—Upper surface: Yellow Group 7A. Lower surface: Yellow Group 7A.

Petals:

*Petal reflex.*—Somewhat reflexed.

*Margin.*—Entire and uniform. Moderate undulations.

*Shape.*—Broad and elliptic. Apex shape: Rounded. Base shape: Acute.

*Size.*—21 mm (l)×27 mm (w).

*Texture.*—Smooth.

*Thickness.*—Average.

Petaloids:

*Size.*—11 mm (l) by 9 mm (w).

*Quantity.*—

*Shape.*—Elliptical with an acute base and rounded apices.

*Color.*—Basal petaloid spots are Yellow Group 7A. On the upper surface Orange-Red Group N30B. Red Group 43C splashed with Red Group 43B on the lower surface.

Reproductive flower parts:

*Pollen.*—None observed.

*Anthers.*—Size: 2 mm in length. Color: Yellow Group 4B. Quantity: 45 on average.

*Filaments.*—Color: Yellow-Orange Group 14B Length: 4 mm.

*Pistils.*—Length: 6 mm. Quantity: 20 on average.

*Stigmas.*—Color: Green-White Group 157A.

*Styles.*—Color: Green-White Group 157A.

*Location of stigmas.*—Superior in location relative to the length of the filaments and the height of the anthers.

*Hips.*—None Observed.

PLANT

Plant growth: Upright, very compact, and well branched. Plants are 39 cm in height, and 25 cm wide.

Stems:

*Color of juvenile growth.*—Yellow-Green Group 144A with intonations of Greyed-Red Group 181B.

*Color of mature growth.*—Yellow-Green Group 147B.

*Length.*—Canes are about 12 cm from the base of the plant to the flowering portion.

*Diameter.*—About 6 mm.

*Internodes.*—On mature canes about 26 mm between nodes.

*Surface texture.*—Young wood: Smooth. Older wood: Smooth.

Long prickles:

*Incidence.*—6 prickles per 10 cm of stem.

*Size.*—Average length of prickles on mature stems is 6 mm.

*Shape.*—Upper portion is linear. Lower portion is linear.

*Color.*—Juvenile prickles: Greyed White 156A. Mature prickles: Greyed White 156A.

Plant foliage:

*Compound leaf.*—70 mm (l)×54 (w).

*Quantity.*—3 leaves per 10 cm of stem on average.

*Leaf bearing angle to the stem.*—45 degrees.

*Color of juvenile foliage*.—Upper side: Yellow-Green Group 144A with intonations of Greyed-Red Group 178A. Lower side: Yellow-Green Group 144A with intonations of Greyed-Red Group 178A.

*Color of mature foliage*.—Upper side: Yellow-Green Group 146A. Lower side: Yellow-Green Group 147C.

Plant leaves and leaflets:

*Stipules*.—Size: 8 mm long, mm wide. Quantity: 2 per compound leaf. Shape: Linear, slightly broad based with outward extending apices. Margins: Finely serrated. Color:.

*Petiole*.—Length: 15 mm. Diameter: 2 mm. Upper surface color: Yellow-Green Group 144A. Lower surface color: Yellow-Green Group 144A.

*Rachis*.—Length: 26 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 26 mm long, 22 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulty025', substantially as illustrated and described herein, due to its abundant orange red flowers, disease resistance, and extended period of bloom.

* * * * *

'Poulty025'

'Poulty025'